United States Patent [19]
Wilson et al.

[11] Patent Number: 5,919,195
[45] Date of Patent: Jul. 6, 1999

[54] OBLONG ACETABULAR COMPONENT INSTRUMENTATION

[75] Inventors: Stephen F. Wilson, Raynham; Farid Bruce Khalili, Chestnut Hills, both of Mass.

[73] Assignee: Johnson & Johnson Professional, Inc., Raynham, Mass.

[21] Appl. No.: 09/009,390

[22] Filed: Jan. 20, 1998

[51] Int. Cl.[6] .................................................. A61B 17/17
[52] U.S. Cl. ................................................ 606/80; 606/81
[58] Field of Search ................................ 606/79, 80, 81, 606/91

[56] References Cited

U.S. PATENT DOCUMENTS

| | | | |
|---|---|---|---|
| D. 296,714 | 7/1988 | Averill et al. | D24/33 |
| 3,744,061 | 7/1973 | Frost | 3/1 |
| 4,611,587 | 9/1986 | Powlan | 606/81 |
| 4,634,444 | 1/1987 | Noiles | 623/20 |
| 4,662,891 | 5/1987 | Noiles | 623/22 |
| 4,678,472 | 7/1987 | Noiles | 623/1.8 |
| 4,695,282 | 9/1987 | Forte et al. | 623/22 |
| 4,704,127 | 11/1987 | Averill et al. | 623/22 |
| 4,712,951 | 12/1987 | Brown | 408/158 |
| 4,798,610 | 1/1989 | Averill et al. | 623/22 |
| 4,846,839 | 7/1989 | Noiles | 623/18 |
| 4,865,603 | 9/1989 | Noiles | 623/18 |
| 4,892,549 | 1/1990 | Figgie, III et al. | 623/22 |
| 4,950,299 | 8/1990 | Noiles | 623/22 |
| 4,978,356 | 12/1990 | Noiles | 623/18 |
| 5,116,165 | 5/1992 | Salyer | 407/54 |
| 5,192,329 | 3/1993 | Christie et al. | 623/22 |
| 5,282,864 | 2/1994 | Noiles et al. | 623/18 |
| 5,290,315 | 3/1994 | DeCarlo, Jr. | 623/22 |
| 5,358,532 | 10/1994 | Evans et al. | 623/22 |
| 5,370,704 | 12/1994 | DeCarlo, Jr. | 623/22 |
| 5,413,603 | 5/1995 | Noiles et al. | 623/18 |
| 5,549,694 | 8/1996 | Noiles et al. | 623/22 |
| 5,549,697 | 8/1996 | Caldarise | 623/22 |
| 5,549,698 | 8/1996 | Averill | 623/22 |
| 5,549,701 | 8/1996 | Mikhail | 623/22 |
| 5,571,201 | 11/1996 | Averill et al. | 623/22 |
| 5,676,704 | 10/1997 | Ries et al. | 623/18 |
| 5,733,289 | 3/1998 | Seedhom et al. | 606/80 |

*Primary Examiner*—Michael Buiz
*Assistant Examiner*—David O. Reip
*Attorney, Agent, or Firm*—Nutter, McClennen & Fish, LLP

[57] ABSTRACT

A system for reaming a cavity in bone for implantation of a prosthetic component, such as an oblong acetabular cup having an outer surface formed by adjacent hemispheres. In one embodiment, the reaming system is useful to form a second cavity in relation to an already formed first cavity. The reaming system includes an instrument with an elongate handle and a drive member coupled to a bearing plate with a locator member removably and replaceably mountable to the bearing plate. The drive member has a distal reamer mating end and a proximal end for coupling with a drill mechanism. The distal reamer mating end is axially movable toward and away from the bearing plate to ream the cavity corresponding to the secondary hemisphere of the acetabular cup to be implanted. In another embodiment, the reaming system includes a plurality of reamers each having different outer dimensions and being matable to the drive member. In a further embodiment, the system includes a plurality of locator members for positioning a respective one of the reamers to form the second cavity at a desired location.

30 Claims, 10 Drawing Sheets

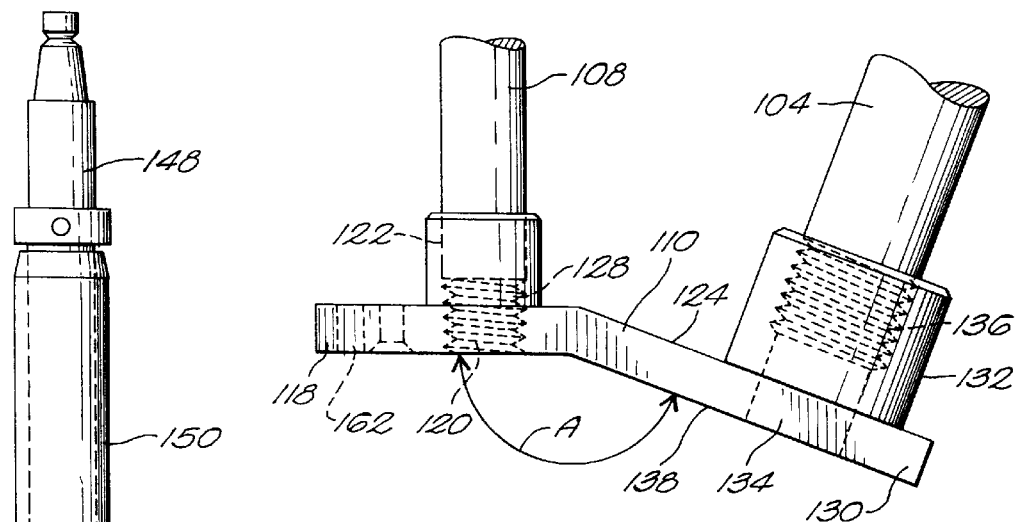
FIG. 10
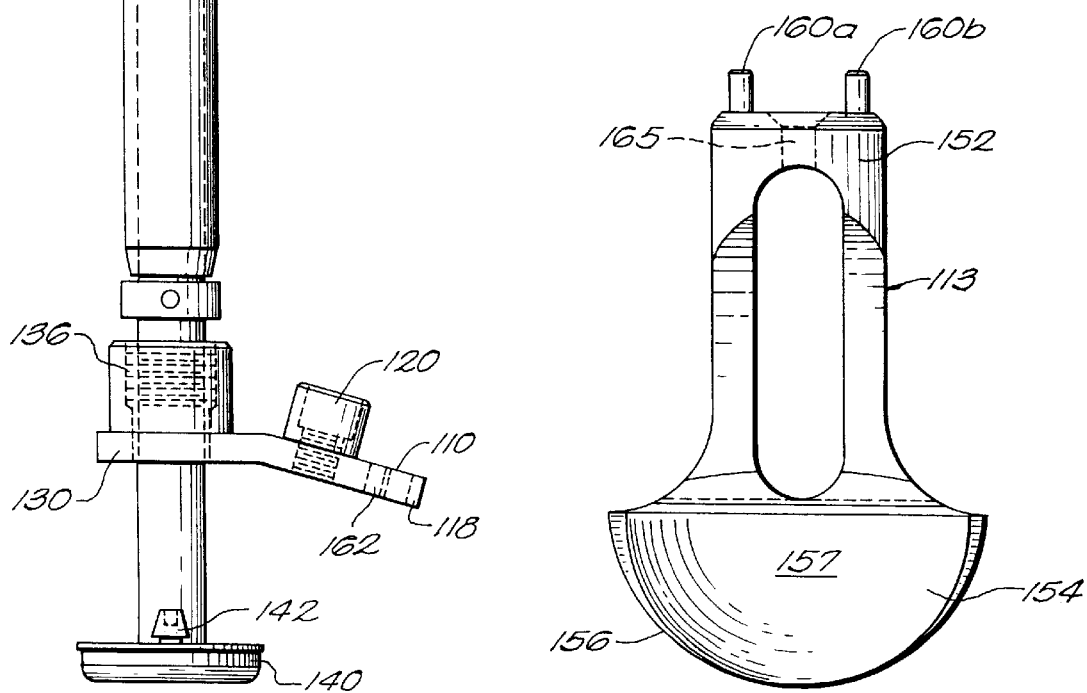
FIG. 9
FIG. 11

OBLONG ACETABULAR COMPONENT INSTRUMENTATION

CROSS REFERENCE TO RELATED APPLICATIONS

Not applicable.

STATEMENT REGARDING FEDERALLY SPONSORED RESEARCH

Not applicable.

FIELD OF THE INVENTION

The present invention relates to reaming systems and more particularly to a system for reaming bone in preparation for implanting a prosthetic component, such as an acetabular cup.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint.

In a total hip arthroplasty an acetabular cup is implanted in the acetabular cavity in the pelvis to replace the natural acetabulum. Replacement of the acetabulum is necessary for various joint conditions, such as when there is an inadequate articulation surface for a head or ball of a prosthetic femoral component. Total hip arthroplasty is also warranted in certain cases of Developmental Displasia Hip (DDH) where the natural acetabular cavity does not properly form to allow sufficient joint articulation.

To implant an acetabular cup, a cavity is reamed in the acetabulum. The acetabular cup is then inserted into the formed cavity and secured by mechanical means, interference fit, or by a combination thereof. The acetabular cup is positioned in the pelvis at a fixed orientation with respect to patient anatomy and should remain stable.

In cases where the acetabular cavity is not generally spherical, an oblong acetabular cup may need to be implanted. Such cases include joint conditions where an implanted acetabular cup (typically a hemispherical cup) has migrated in a superior direction and certain DDH cases. The oblong geometry of the cup compensates for the elongated acetabular cavity. One type of elongated acetabular cup has an outer contour defined by two adjacent hemispheres. An exemplary dual hemisphere acetabular cup 10 is shown in FIGS. 1A and 1B. The cup 10 has an outer surface 12 defined by a first primary hemisphere 14 merged with a secondary hemisphere 16. The primary hemisphere defines a primary face 18 and the secondary hemisphere defines a secondary face 19. The primary hemisphere 14 has a concave inner surface 17 adapted for receiving the liner capable of receiving head or ball of a femoral component.

If such an oblong acetabular cup is to rely on an interference fit alone to secure the prosthesis, it is important that the cavity be formed within precise dimensional tolerances. If a proper fit is not achieved, long term fixation of an interference fit acetabular cup in the acetabulum will not occur. However, using conventional instrumentation it is difficult to achieve the required level of precision when reaming the acetabular cavity.

To implant the oblong acetabular cup, the cavity in the acetabulum is typically formed in two discrete stages. First, the true (also known as primary or natural) acetabular cavity is formed. Generally, a surgeon aligns a conventional reamer/driver instrument with the acetabulum and reams the primary or natural acetabular cavity to a hemispherical shape. FIG. 2 shows an illustrative prior art reamer/driver instrument 20 for reaming the natural acetabular cavity 22 in the acetabulum 24. Forming the natural acetabular cavity with the reamer/driver instrument 20 is a relatively straight forward process. However, to form the false or defect cavity for an oblong cup 10, the already formed natural cavity 22 should be used as a reference point to provide a cavity that matches the outer surface 12 of the oblong cup 10.

FIG. 3 shows one type of prior art instrument, known as a basket reamer/driver 30, used to form the false acetabular cavity after reaming the true acetabular cavity. As used herein, reamer/driver refers to an instrument as a whole, while reamer refers to the rotating head for removing tissue. The device 30 includes an arcuate guide 32 for placement in the reamed natural cavity and a reamer 34 for removing bony tissue. The reamer 34 is matable with a power drill mechanism for rotating the reamer.

To form the false acetabular cavity, the surgeon first visually identifies the location where the false cavity is to be formed. The false or defect cavity will be somewhere about the periphery of the natural acetabular cavity 22 (FIG. 2). After placing the guide 32 in the reamed natural cavity, the surgeon rolls the reamer 34 in a direction toward the area to be reamed to form the false acetabular cavity. However, it is difficult to retain alignment of the instrument relative to the acetabulum as the reamer is rolled to form the defect cavity. Further, it is not readily apparent when the desired amount of bone has been removed. Thus, it is difficult to form a dual hemisphere acetabular cavity with the requisite precision for long term fixation of an oblong interference fit acetabular cup.

Another drawback associated with known basket reamer/driver instruments is the lack of modularity among the various components. In general, a cavity is reamed using sequentially larger reamers. However, each reamer is adapted for coupling to a particular reamer/driver instrument sized to receive the given reamer. Thus, as a reamer/driver provides only one sized cavity, several reamer/driver instruments are needed to prepare an acetabular cavity in the acetabulum.

It would be desirable to provide a modular reaming system for forming a compound geometry cavity that precisely conforms to the outer surface of an oblong acetabular cup.

SUMMARY OF THE INVENTION

The present invention provides a reaming system for precise formation of a cavity having a compound geometric shape. Although the invention is primarily shown and described in conjunction with reaming an acetabulum for implanting an oblong acetabular cup, it is understood that the invention has other applications as well.

In one embodiment, the reaming system is particularly useful in forming a second cavity in the acetabulum in relation to a first cavity for implantation of an acetabular cup with a dual hemisphere outer surface. The reaming system includes a reamer/driver instrument with a bearing plate having a first portion coupled to the distal end of a handle and a second portion coupled to an elongate drive member. A proximal end of the handle facilitates positioning of the instrument. The drive member has a distal reamer mating end and a proximal end for coupling with a mechanism to rotate the distal reamer mating end of the drive member. The distal reamer mating end is axially movable toward and away from a distal surface of the bearing plate to form the second cavity. The system further includes at least one locator member removably and replaceably mountable to the distal surface of the bearing plate for positioning the distal reamer mating end in relation to the already formed first cavity.

In a further embodiment, the system includes a plurality of reamers each having different outer dimensions and an inner surface matable with the distal reamer mating end of the single drive member. The reamers and drive member provide a modular reaming system allowing incremental increases in the size of the cavity by sequentially attaching reamers of increasing outer dimensions to the drive member.

In a still further embodiment, the reaming system includes a plurality of locator members each having a geometry corresponding to a particular size reamer. In an exemplary embodiment, each of the locator members has a base portion matable to a bearing plate and an upper portion with an outer surface, at least part of which forms a part of a sphere. The arcuate outer surface is adapted for placement within the hemispherical inner surface of the already formed first cavity. Each locator member has a geometry that is effective to position a particular reamer such that the second cavity is formed to complement a corresponding portion of the oblong acetabular cup to be implanted.

In another embodiment, the system includes a guide member that is securable to the handle to provide an indication of the abduction and anteversion angle of the drive member in relation to the patient. In an exemplary embodiment, the guide member has a leg portion with first and second arm portions extending from one end of the leg portion. The other end of the leg portion is matable with the handle such that the guide member is rotatable about the longitudinal axis of the handle. The orientation of the leg and arm portions of the guide member in relation to the patient provides a visual indication of the respective abduction and anteversion angles at which the second cavity will be reamed.

The instrument is assembled by selecting a reamer to form a second cavity of desired size and securing the reamer to the distal reamer mating end of the drive member. A corresponding locator member is then affixed to the bearing plate. The guide member is mated to the handle and the proximal end of the drive member is coupled to a drill mechanism.

To form the cavity, the locator member is positioned in the already formed first cavity. The guide member provides a visual indication of the abduction and anteversion position of the instrument in relation to the patient. As is known to one of ordinary skill in the art, the abduction angle is measured with respect to the transverse plane which divides the body into superior and inferior portions. The anteversion angle is measured with respect to the coronal or frontal plane to form a boundary between anterior and posterior portions of the body. In one embodiment, the instrument is positioned at a predetermined abduction angle when the leg portion of the guide member is vertical as the patient lay horizontally. The instrument is positioned at a predetermined anteversion angle when the longitudinal axis of the drive member is aligned with a tip of either the first or second arm portions of the guide member.

The location at which the second or defect cavity is to be formed is then determined by the surgeon. The instrument is rotated about the first or true acetabular cavity (with the locator member in the first cavity) while maintaining the abduction and anteversion orientation of the instrument. The guide member is rotatable about the longitudinal axis of the handle to facilitate positioning of the instrument to ream the second cavity while maintaining the alignment of the face of the primary hemisphere of the implant. After the instrument is positioned, the drive member is moved axially in a direction away from the bearing plate for removing tissue to form the defect cavity. A compound geometry cavity is thereby precisely formed in the acetabulum for receiving a dual hemisphere acetabular component.

BRIEF DESCRIPTION OF THE DRAWINGS

The invention will be more fully understood from the following detailed description in conjunction with the accompanying drawings, in which:

FIG. 9 is a front view of a drive member forming a portion of the reaming system of FIG. 4A;

FIG. 10 is a side view of a bearing plate forming a portion of the reaming system of FIG. 4A;

FIG. 11 is a side view of a locator member forming a portion of the reaming system of FIG. 4A;

DETAILED DESCRIPTION OF THE INVENTION

Figure 1A:
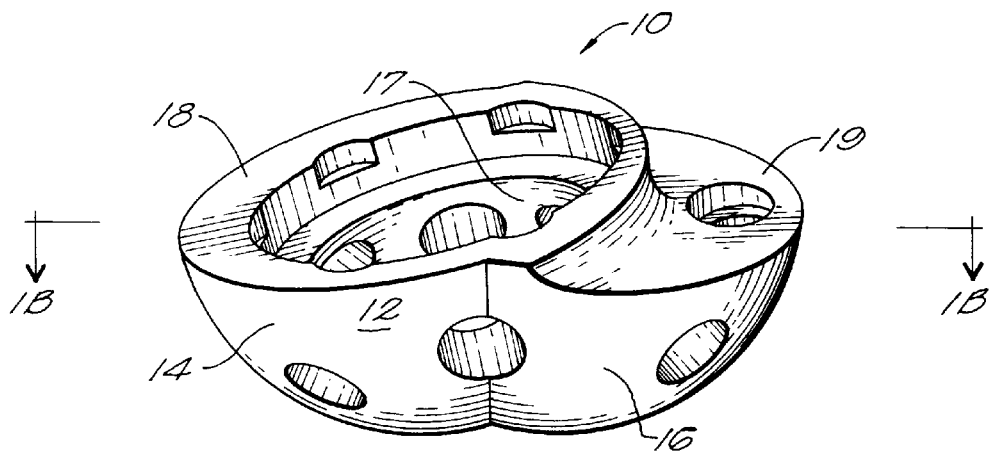
FIG. 1A is a perspective view of a prior art oblong acetabular cup.
Figure 1B:
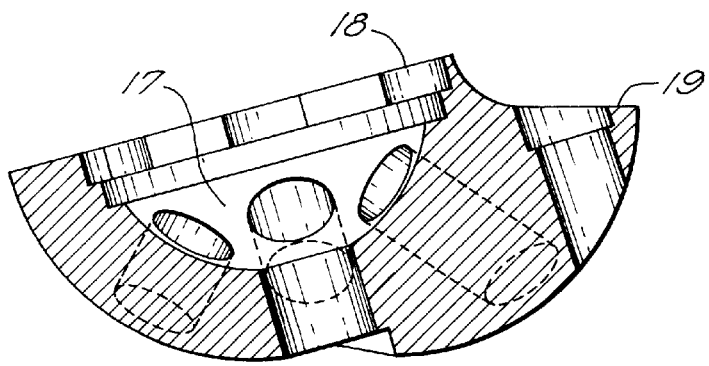
FIG. 1B is a cross-sectional view of the prior art acetabular cup of FIG. 1A along lines 1B—1B.
Figure 3:
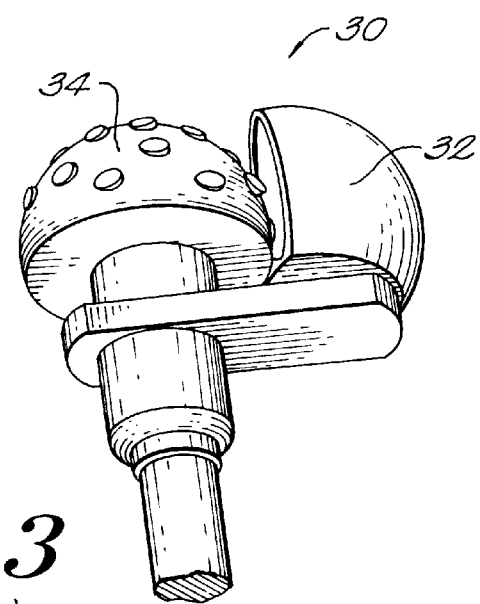
FIG. 3 is a perspective view of a prior art basket reamer.

FIGS. 4A–11 illustrate an exemplary reaming system 100 including an instrument 102 having a drive member 104 matable with a reamer 106 and an elongate handle 108 coupled to a bearing plate 110. A locator member 113 extends from the bearing plate 110 for insertion into an already formed cavity to position the instrument 102. As described below, the reaming system 100 is particularly useful in forming a false or defect acetabular cavity in the acetabulum 24 in relation to an already formed primary cavity 22 for implanting an oblong acetabular cup 10 (FIG. 1).

The handle 108 has a proximal end 112 with a hand grip 114 to facilitate positioning of the instrument 102. A distal end 116 of the handle is secured to a first portion 118 of the bearing plate. The handle 108 can be coupled to the bearing plate 110 using a variety of engagement mechanisms that can provide releasable or permanent engagement, and combinations thereof. In one embodiment, the distal end 116 of the handle is insertable into a bore 120 (FIG. 8) formed in a handle engaging portion 122 extending from a proximal surface 124 of the bearing plate. Threads 126 formed on the distal end 116 of the handle are engageable with threads 128 formed on the inner surface of the bore for threadably engaging the handle 108 to the bearing plate 110.

The bearing plate 110 has a second portion 130 with a drive member guide portion 132 extending from the proximal surface 124 of the bearing plate. A bore 134 (FIG. 8) extends through the drive member guide portion 132 with a bearing 136 (FIG. 10) disposed at least partly within the bore. The drive member guide portion 132 and bearing 136 secure the drive member 104 at a fixed angle with respect to the handle 108 while allowing axial and rotational movement of the drive member with respect to the bearing plate 110.

As shown in FIG. 10, the second portion 130 of the bearing plate extends from the first portion 118 at an angle A. The angled bearing plate 110 positions the handle 108 and drive member 104 at angle A. This angle corresponds to the angle formed by the primary and secondary faces of the acetabular component, as described below. The angle A of the bearing plate first and second portions 118,130 can vary from about zero to about forty-five degrees, and more preferably from about fifteen degrees to about twenty degrees.

Figure 8:
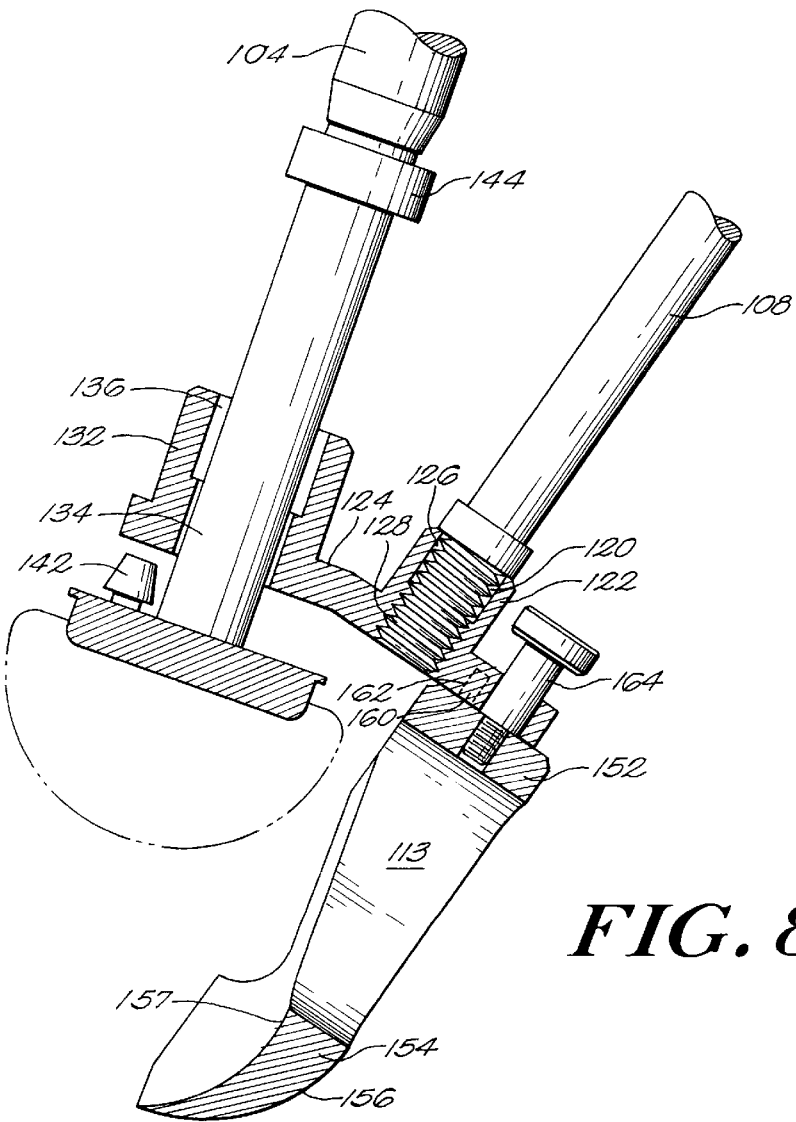
FIG. 8 is a side view in partial cross-section of a distal portion of the reaming system of FIG. 4A.

The drive member 104 has a distal reamer mating end 136 that extends from a distal surface 138 of the bearing plate. The reamer 106 is selectively matable to the distal end 136 such that the reamer can be quickly engaged and released from the drive member 104. In the exemplary embodiment shown herein, the distal reamer mating end 136 terminates in an annular mounting plate 140 that is readily engagable with the reamer 106. The reamer 106 is mounted on the plate 140 by applying axial pressure and released by actuating a biased release switch 142 (FIG. 8). It is understood, however, that one of ordinary skill in the art can readily modify the reamer mating mechanism 140,142 described herein.

A collar 144 is affixed to the drive member 104 at a predetermined distance from the tip of the distal reamer mating end 136. The collar 144 is effective to limit axial movement of the distal reamer mating end 136 in a direction away from the distal surface 138 of the bearing plate. More particularly, at maximum extension of the reamer 106 (FIG. 4B) the collar 144 abuts the drive member guide portion 132 of the bearing plate. At full retraction of the reamer 106 (FIG. 4A), the collar 144 is located at a selected distance from the drive member guide portion 132 and the distal reamer mating end 136 of the drive member is adjacent the bearing plate 110.

The proximal end 146 of the drive member is adapted for coupling with a conventional drill mechanism (not shown) to rotate the drive member 104 and reamer 106. Such drill mechanisms are well known to one of ordinary skill in the art.

The drive member 104 can include various components to enable rotation and distal extension of the reamer 106 while maintaining the drive member at a fixed angle relative to the bearing plate 110 and the handle 108. In the exemplary embodiment shown in FIG. 9, the drive member 104 includes an inner member 148 that is rotable within a concentric outer member 150.

Referring in particular to FIGS. 5A–B, 8, and 11 the locator member 113 has a base portion 152 that is matable to the distal surface 138 of the bearing plate 110 and an upper portion 154 with an outer surface 156 shaped to complement the formed true acetabular cavity. As described in further detail below, the locator member 113 positions the reamer 106 such that the false acetabular cavity is formed by referencing the location of the already formed by true acetabular cavity. In an exemplary embodiment, the outer surface 156 of the locator member forms a portion of a sphere that complements the spherical cavity formed the reamer 106. In one embodiment, the longitudinal axis of the handle 108 is aligned with the center of the spherical shape partially formed by the outer surface 156 of the locator member.

The upper portion 154 of the locator member also includes an arcuate inner surface 157. The inner surface 157 is generally concave such that the locator member 113 does not interfere with the reamer 106. It is important that the reamer 106 be axially extendable from the bearing plate 110 without contacting the locator member 113. The inner surface 157 should be dimensioned to provide adequate spacing from the reamer 106 to allow removed tissue to escape from the rotating reamer.

The base portion 152 of the locator member has an end surface 158 with first and second posts 160a,b (FIG. 11) extending therefrom. The posts 160 are insertable within corresponding first and second bores 162 formed in the first portion 118 of the bearing plate 110. The posts 160 are precisely located to position the outer surface 156 of the locator member in relation to the drive member 104 and reamer 106.

The locator member 113 can be secured to the bearing plate 110 with a variety of attachment mechanisms. Exemplary mechanisms include fasteners such as nuts, bolts, screws, interference fit dimensions and other detachable mechanisms. In the exemplary embodiment shown, the locator member 113 is securable to the bearing plate with a retaining screw 164 passing through an aperture in the bearing plate 110 into a corresponding threaded bore 165 in the locator member 113.

The reaming system 100 can also include a guide mechanism 166 for providing anteversion and abduction information to an operator. In an exemplary embodiment, the guide mechanism 166 has a guide member 168 with a leg 170 and first and second arms 172a,b forming a V-shape. As shown, the arms 172 are perpendicular to the leg portion 170. A distal end 174 of the leg is insertable into a bore formed in an alignment block 176 coupled to the handle 108. The alignment block 176 is rotatable about a longitudinal axis of the handle 108 when positioning the reamer to form the defect cavity, as described below.

The bore in the alignment block 176 is formed such that the leg 170 extends from the alignment block to form an angle C (FIG. 5A) of about one hundred and thirty-five degrees with respect to the handle. When the arms 172 are horizontal as the patient lay on the operating table, the exemplary desired abduction angle of about forty-five degrees is achieved. As is known to one or ordinary skill in the art, the abduction angle is determined with respect to the midline transverse plane.

Figure 7:
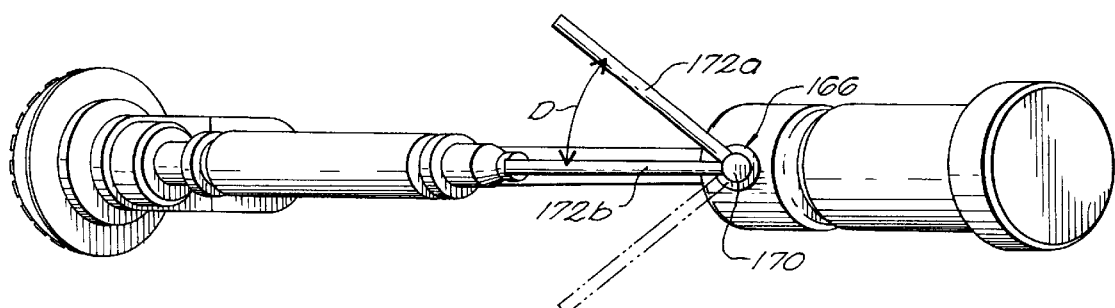
FIG. 7 is a top view of the reaming system of FIG. 4A.

As shown in FIG. 7, the first and second arms 172a,b of the guide form an exemplary angle D of about forty degrees. The angle D is bifurcated into two twenty degree sections to provide an anteversion angle of about twenty degrees when forming the false acetabular cavity. As is known to one of ordinary skill in the art, the anteversion angle is measure with respect to the coronal or frontal plane. The arms 172 serve as guides for the operator when orienting the reamer/driver. More particularly, the drive member 104 is axially aligned with an end of one of the arms 172 to provide about twenty degrees of anteversion when forming the false acetabular cavity.

Figure 12:
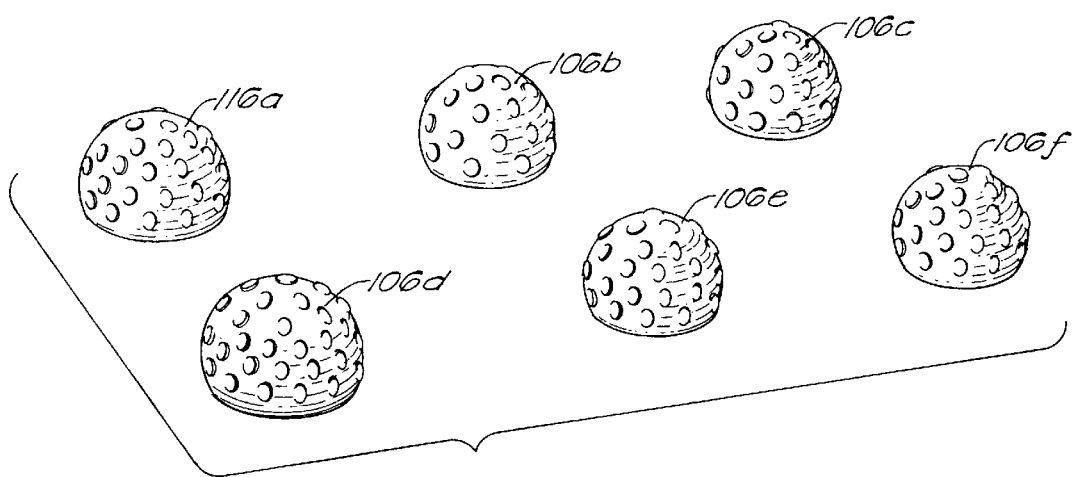
FIG. 12 is a perspective view of a series of reamers forming a portion of a further embodiment of a reaming system in accordance with the present invention.

In another embodiment shown in FIG. 12, the reaming system 100 of the present invention includes a series of different sized reamers 106a–f to provide a modular system. Each of the reamers 106 has outer dimensions for reaming a particular sized cavity. The reaming system 100 requires a single reamer/driver instrument 102 that is matable to each of the reamers 106. Thus, the reamer/driver is not limited to forming a certain size cavity, as in prior art reaming devices.

Figure 13:
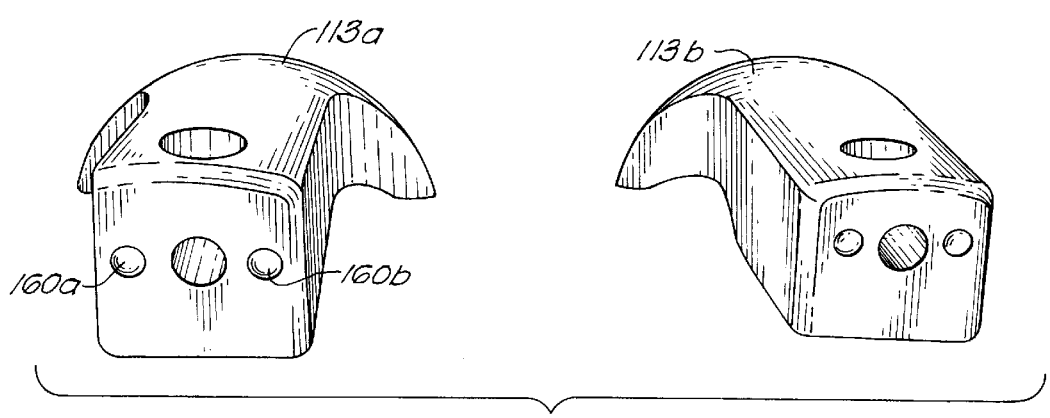
FIG. 13 is a perspective view of a series of locator members forming a portion of another embodiment of a reaming system in accordance with the present invention.

As shown in FIG. 13, the system 100 can also include a series of locator members 113a,b differing in size. Although two locator members 113 are shown, it is understood that the system can include any number of reamers and locator members. Each locator member 113 corresponds to a particular size acetabular component to be implanted and/or reamer 106 to be used to form the false acetabular cavity. As the dual hemisphere acetabular component increases in size, the corresponding locator member 113 also increases in size to position the reamer 106 to the desired location. That is, for each size acetabular cup implant, the corresponding locator member 113 provides a reference point for forming the false acetabular cavity in relation to the reamed true acetabular cavity.

Due to the geometry of the locator members 113, the collar 144 does not need to be adjusted for each reamer or acetabular cup. The locator members 113 are formed such that the maximum reamer extension determined by the collar 144 corresponds to the depth desired for the selected reamer and acetabular cup.

The overall dimensions for reamer/driver and various components can vary to achieve a desired geometry for the natural and defect cavities to conform to the outer surface of a particular acetabular component. It is understood that one of ordinary skill in the art can readily modify the exemplary shape and dimensions described herein.

Illustrative radii for the outer surface of the reamers 106 include 45, 48, 51, 54, 57, 60, and 63 millimeters. The corresponding locator members 113 have a spherical outer surface 156 formed by a radius that can range from about 20 millimeters to about 40 millimeters.

It is understood that the dimensions described above are illustrative and that one of ordinary skill in the art can readily modify the particular embodiments shown and described herein without departing from the scope and spirit of the invention.

The dual geometry acetabular cavity is prepared to receive the acetabular component in an exemplary sequence of steps. The acetabular area of the patient is first evaluated using X-rays to determine the acetabular configuration and to reveal any anatomical anomaly, dysplasia, and/or leg-length discrepancy. Preoperative templating can then be performed to determine the size of the acetabular component to be implanted.

Figure 2:
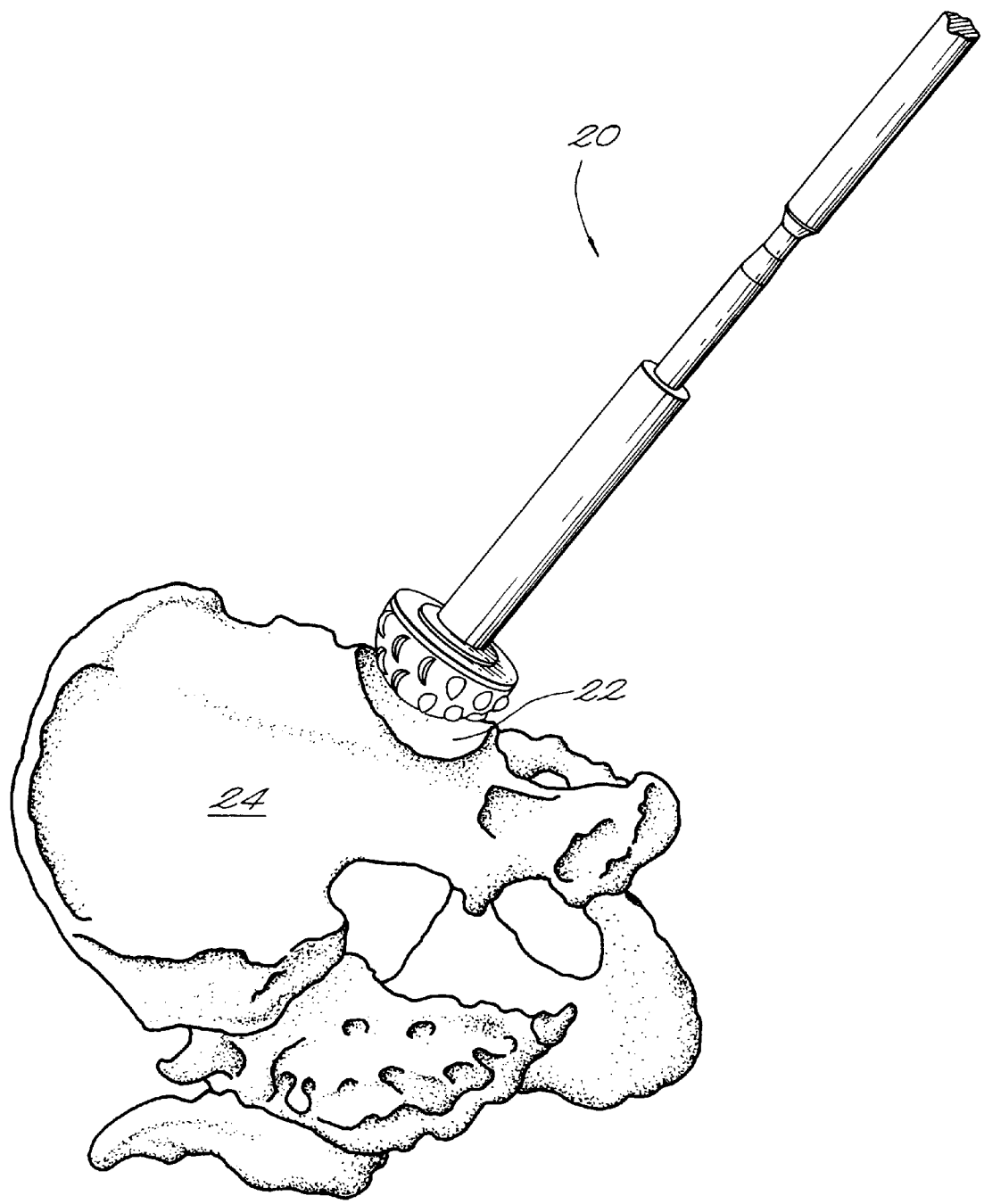
FIG. 2 is a perspective view of a prior art reamer/driver instrument.
Figure 4A:
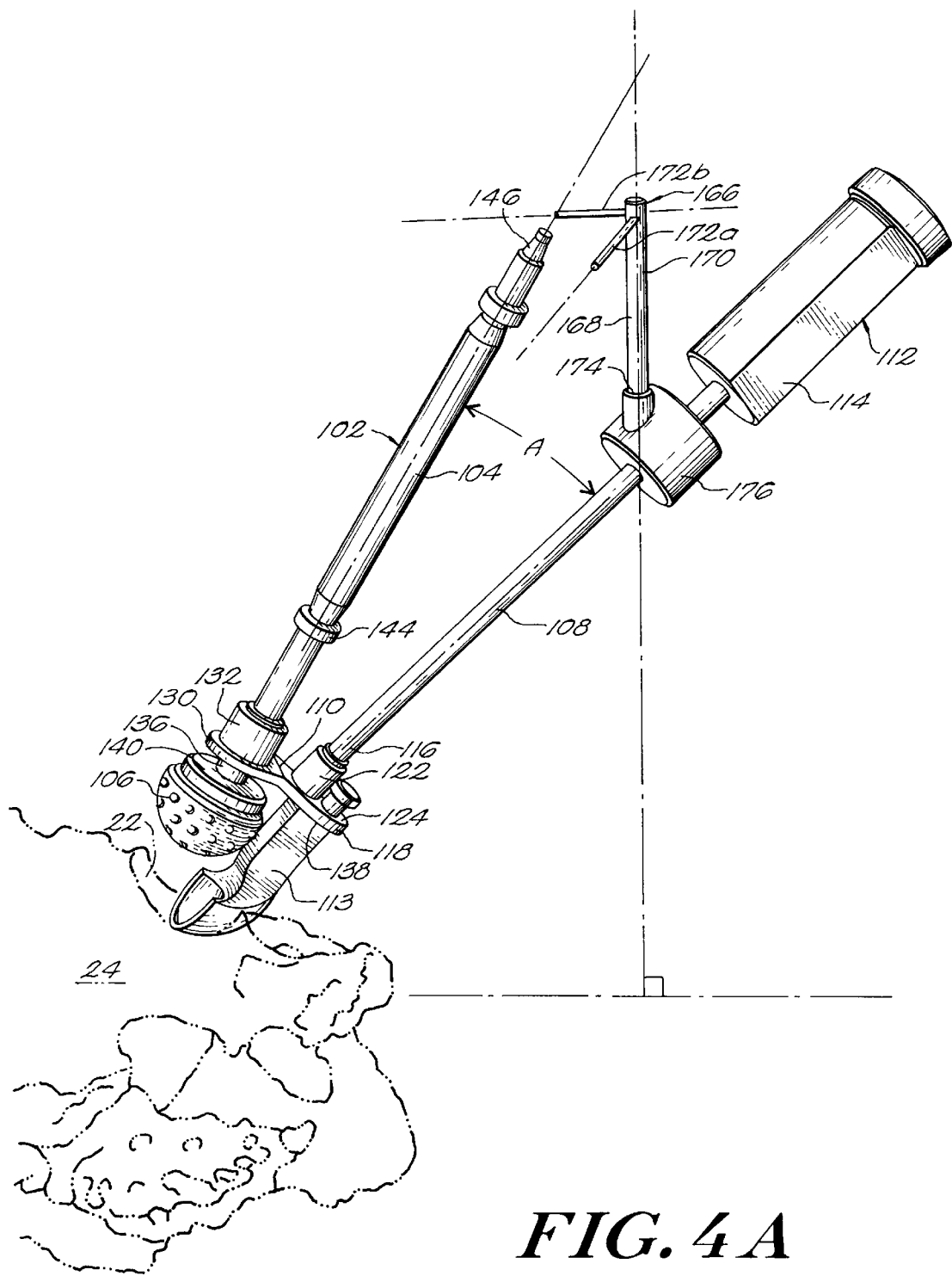
FIG. 4A is a perspective view of a reaming system in accordance with the present invention shown in a first position.
Figure 4B:
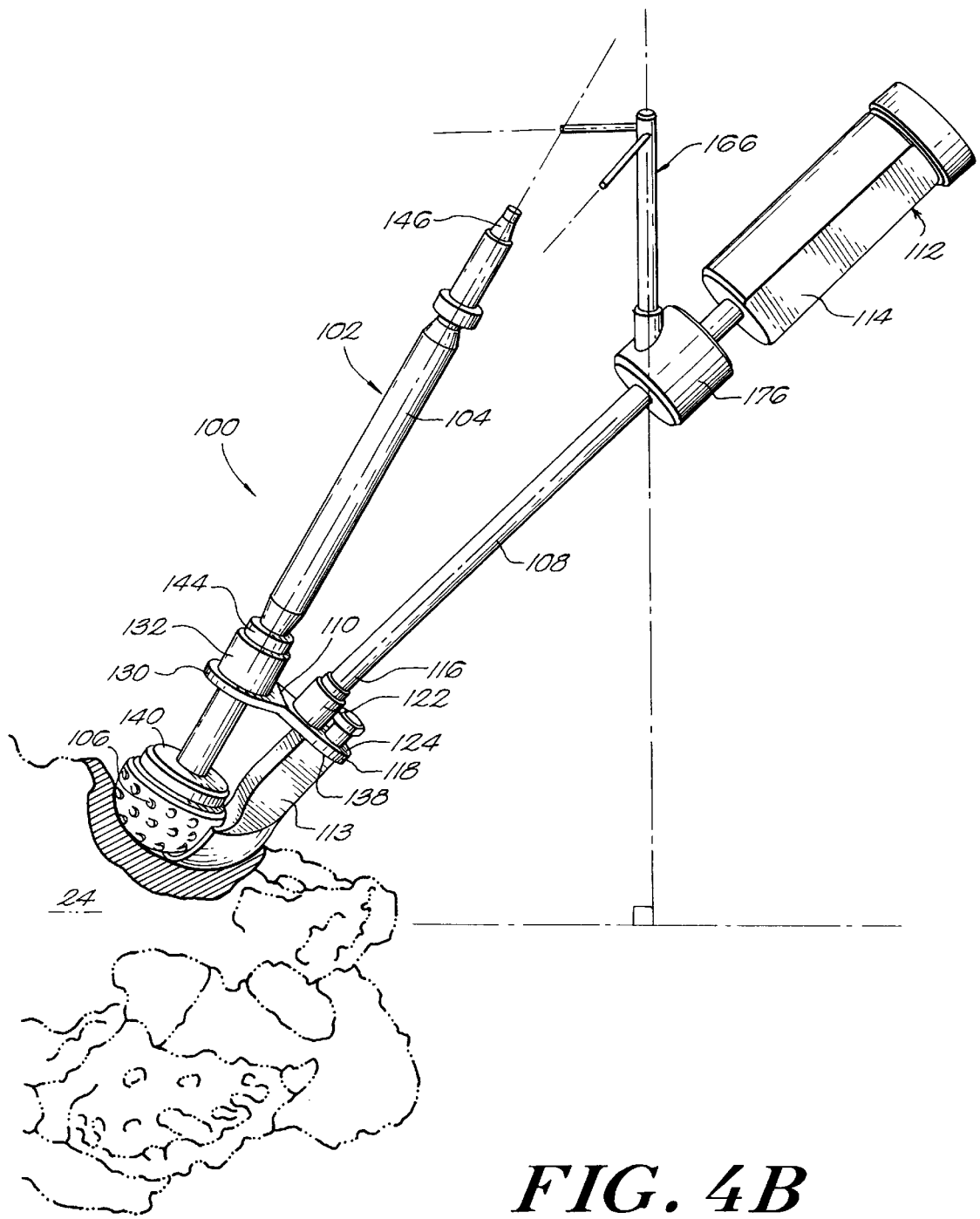
FIG. 4B is a perspective view of the reaming system of FIG. 4A shown in a second position.
Figure 5A:
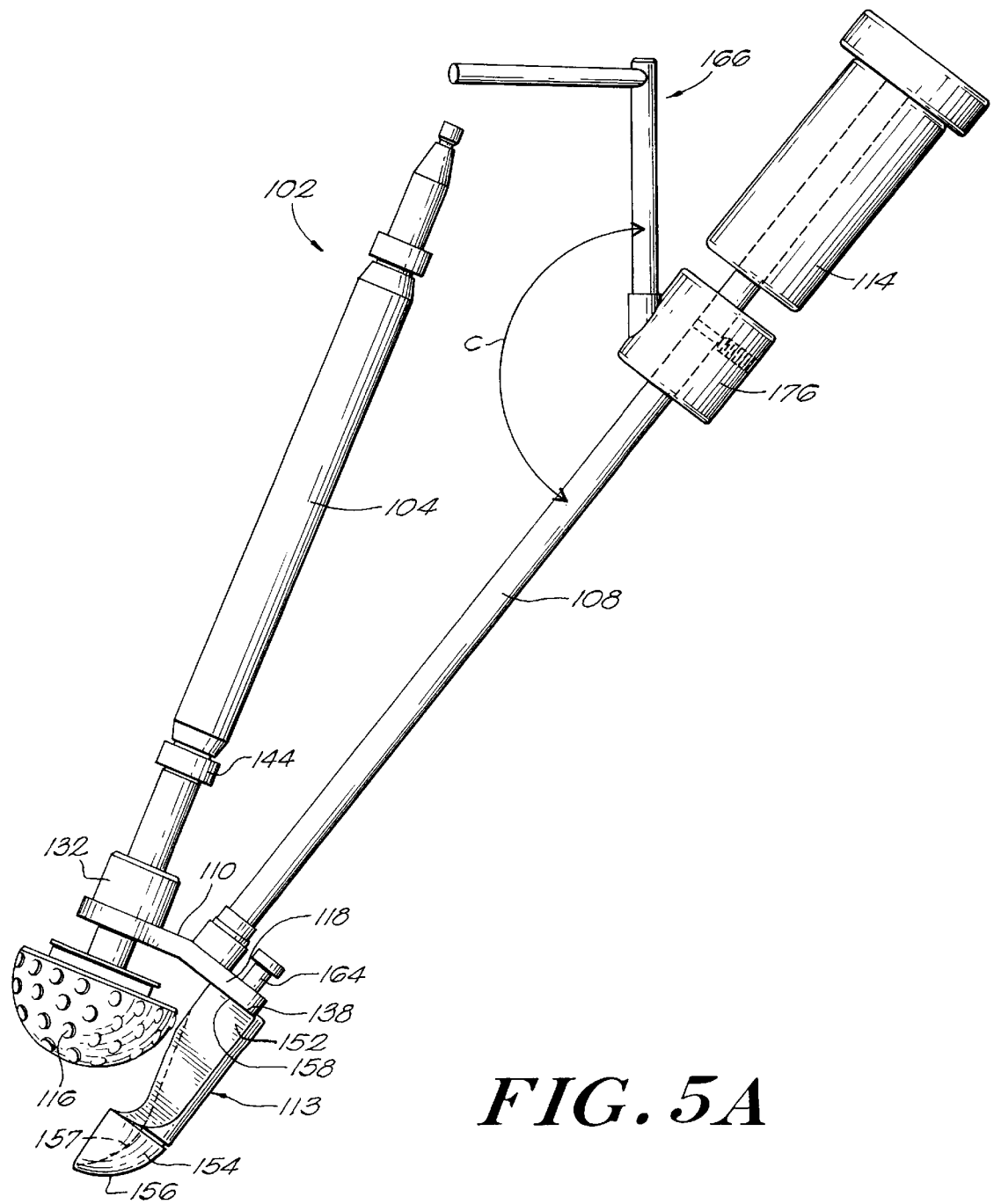
FIG. 5A is a side view of the reaming system of FIG. 4A shown in the first position.
Figure 5B:
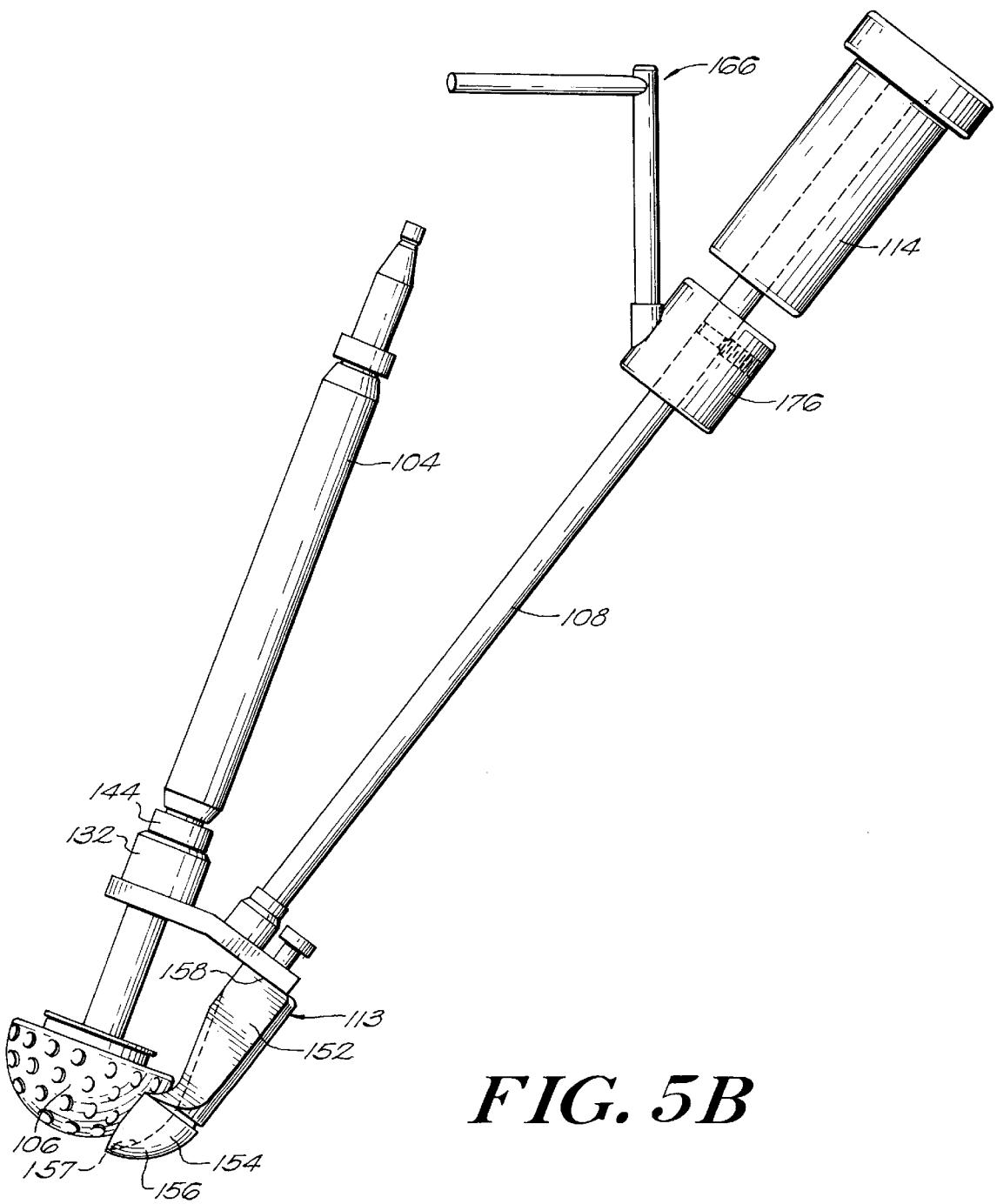
FIG. 5B is a side view of the reaming system of FIG. 4A shown in the second position.
Figure 6:
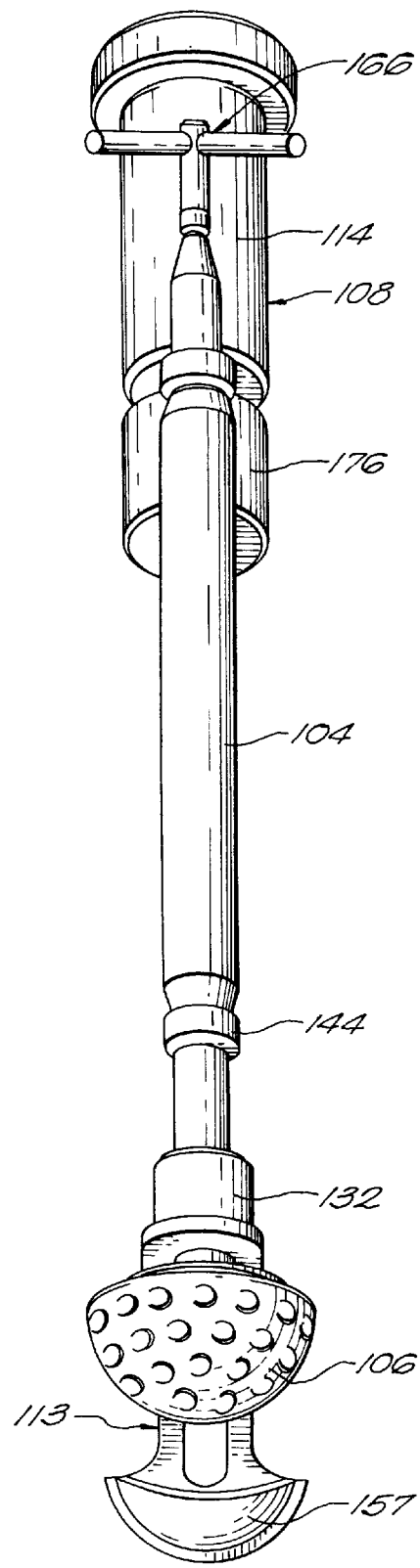
FIG. 6 is a front view of the reaming system of FIG. 4A.

To form a cavity conforming to the compound geometry of the oblong acetabular cup, two discrete reaming steps are performed. First the natural or true acetabular cavity 22 is formed in the acetabulum 24 (FIG. 2). This cavity is reamed using a conventional reamer/driver instrument 20 well known to one of ordinary skill in the art. The formed natural acetabular cavity 22 has a hemispherical shape for receiving a corresponding primary portion of the oblong acetabular cup.

The false or defect acetabulum cavity is formed using the reaming system 100 of the present invention. The false acetabular cavity corresponds to the secondary or elongated portion 16 of the oblong acetabular implant 10 (FIG. 1). The false acetabular cavity should be positioned in relation to the already reamed natural acetabular cavity and formed within precise dimensional tolerances. Proper location and geometry of the false acetabular cavity provide a secure interference fit for the implant to allow long term fixation of the implanted acetabular cup.

Based on the size of the oblong acetabular cup to be implanted, a corresponding reamer 106 and locator 113 are selected and secured to the instrument 102, as described above. The location of the false acetabular cavity to be formed is then visually determined by the surgeon.

It is understood that the orientation of the true acetabular cavity must be formed such that the primary portion 14 of the acetabular cup is properly aligned to receive the head of the femoral component. The acetabular cup 10 should be implanted to provide optimal range of motion for the femur of the patient and to reflect anatomical joint articulation to the extent possible. Thus, the false acetabular cavity should be formed to receive the secondary portion 16 of the oblong acetabular cup by referencing the true acetabular cavity.

The instrument 102 is positioned in relation to the already formed natural acetabular cavity by placing the locator member 113 within the formed natural acetabular cavity 22. Using the guide 166, the instrument is manipulated to a position of about forty-five degrees abduction and about twenty degrees anteversion. More particularly, the leg member 170 of the guide should extend vertically (FIG. 5A) and the first or second arm 172a,b of the guide should be aligned with the longitudinal axis of the drive member 104 (FIG. 7).

While maintaining the desired anteversion and abduction orientation, the handle 104 is rotated about the true acetabular cavity until the reamer 106 is aligned with the desired location for the false acetabular cavity. During rotation, the alignment block 176 rotates about the handle 106 to allow the anteversion/abduction orientation to be maintained, i.e., to retain the orientation of the primary face of the oblong implant. The spherical outer surface 156 of the locator member easily rotates in the formed spherical natural acetabular cavity to provide a reference point for reaming the false acetabular cavity.

At this point, the instrument 102 has the desired anteversion and abduction orientation and the reamer 106 is aligned with the location of the false acetabular cavity to be formed. The drive mechanism (not shown) is then activated to rotate the drive member 104 and reamer 106. The operator applies axial pressure to the drive member 104 to cause the reamer 104 to extend in a distal direction along the longitudinal axis of the drive member, i.e., away from the bearing plate 110. The anteversion/abduction position of the instrument 102 is maintained during the reaming process. The reamer 106 continues to extend distally until the collar 144 contacts the drive member guide portion 132 of the bearing plate. The plunger-type movement of the reamer 106 forms a false acetabular cavity with a precise depth and contour.

The compound geometry cavity is then evaluated using a oblong trial implant and the acetabular cup is inserted into the formed cavity using known surgical procedures.

One of ordinary skill in the art will realize further features and advantages of the invention from the above-described embodiments. Accordingly, the invention is not to be limited by what has been particularly shown and described, except as indicated by the appended claims. All publications and references cited herein are expressly incorporated herein by reference in their entirety.

What is claimed is:

1. A reaming system for forming a second cavity in relation to a first cavity, comprising:

an elongate handle having a proximal end and a distal end;

a bearing plate having a first portion coupled to the handle and a second portion, the bearing plate further including a proximal surface and a distal surface;

at least one locator member removably and replaceably mountable to the bearing plate;

an elongate drive member coupled to the second portion of the bearing plate, the drive member having a distal reamer mating end and a proximal end for coupling with a drive mechanism to rotate the drive member, the distal reamer mating end being axially movable toward and away from the distal surface of the bearing plate; and a mounting plate disposed at the distal end of the drive member, the mounting plate being matable with the reamer.

2. The system according to claim 1, further including a plurality of reamers, each reamer having different outer dimensions and each having an inner surface matable with the distal reamer mating end of the drive member.

3. The system according to claim 2, wherein at least one of the plurality of reamers has a generally hemispherical outer surface.

4. The system according to claim 2, wherein a plurality of different sized locator members is provided.

5. The system according to claim 4, wherein each of the plurality of locator members has a geometry corresponding to a respective one of the plurality of reamers for positioning the reamer in a desired location.

6. The system according to claim 1, wherein the locator member has a proximal portion matable to the bearing plate and a distal portion with an outer surface, at least a part of which is of a generally spherical shape.

7. The system according to claim 6, wherein a longitudinal axis of the handle is aligned with a center of the spherical shape.

8. The system according to claim 6, wherein the proximal portion of the locator member includes at least one mounting post insertable into a bore formed in the bearing plate.

9. The system according to claim 1, further including a collar affixed to the drive member for limiting movement of the distal reamer mating end of the drive member away from the distal surface of the bearing plate.

10. The system according to claim 9, wherein the collar abuts the proximal surface of the bearing plate at maximum extension of the distal end of the drive member from the bearing plate.

11. The system according to claim 1, further including a guide member securable to the handle for providing abduction and anteversion angles of the reamer in relation to a patient.

12. The system according to claim 11, wherein the guide member includes a leg portion with a first end that is matable to the handle and a second end from which first and second arm portions extend.

13. The system according to claim 12, wherein the first and second arm portions are generally perpendicular to the leg portion.

14. The system according to claim 12, wherein the first and second arm portions form an angle that is proportional to a selected anteversion angle for the second cavity.

15. The system according to claim 12, wherein the leg portion of the guide is effective to form an angle with the handle that corresponds to a predetermined abduction angle for the second cavity.

16. The system according to claim 12, wherein the handle further includes a rotatable member matable with the first end of the guide member leg portion, the rotatable member being affixed to an intermediate portion of the handle and selectively rotatable about a longitudinal axis of the handle.

17. The system according to claim 16, wherein the guide member is rotatable about the handle such that each of the first and second arm portions are positionable with respect to the longitudinal axis of the drive member.

18. The system according to claim 1, wherein the second portion of the bearing plate extends from the first portion of the bearing plate at an angle of about five degrees to about forty-five degrees.

19. The system according to claim 18, wherein the angle formed by the handle and drive member substantially corresponds to the angle formed by the first and second portions of the bearing plate.

20. The system according to claim 1, wherein the handle and the drive member form an angle between about zero degrees and about forty-five degrees.

21. A reaming system for forming a second cavity in relation to an already formed first cavity, comprising:

an elongate drive member having a proximal end for coupling with a drive mechanism and a distal end having a mounting plate, the mounting plate being matable with each of a plurality of reamers for forming the second cavity, wherein each reamer forms a different sized cavity;

a bearing plate having proximal and distal surfaces with an aperture extending therebetween, the bearing plate further including first and second portions angled with respect to each other, wherein a portion of the drive member is secured within the bore to position the drive member with respect to the bearing plate;

a handle having a proximal end for manipulation by a user and a distal end secured to the bearing plate; and at least one locator member selectively matable to the second portion of the bearing plate, the locator member providing a reference point for positioning the reamer in relation to the first cavity.

22. The system according to claim 21, wherein each of the plurality of reamers has a different radius.

23. The system according to claim 21, wherein the locator member includes a base portion with a post extending therefrom for insertion into a corresponding bore formed in the bearing plate and an upper portion with an outer surface having a contour adapted for complementing the shape of the first cavity.

24. The system according to claim 23, wherein the outer surface of the locator member forms a portion of a sphere.

25. The system according to claim 24, wherein a longitudinal axis of the drive member is substantially aligned with a center of the sphere partially formed by the outer surface of the locator member.

26. The system according to claim 21, wherein the locator member is dimensioned in relation to the size of a respective one of the plurality of reamers.

27. The system according to claim 21, further including a plurality of locator members, each having a geometry that is effective to position a respective one of the plurality of reamers in relation to the first cavity.

28. The system according to claim 27, wherein each of the plurality of locator members has an outer surface forming a portion of a sphere and a center of each locator member is aligned with the longitudinal axis of the drive member when secured to the bearing plate.

29. The system according to claim 21, wherein the distal end of the drive member is axially movable between a first position proximate the bearing plate and a second position a selected distance from the bearing plate.

30. The system according to claim 21, further including a collar affixed to the drive member for limiting movement of the distal end of the drive member away from the bearing plate.

* * * * *